(12) United States Patent
Sodroski et al.

(10) Patent No.: US 6,716,429 B1
(45) Date of Patent: Apr. 6, 2004

(54) STABILIZATION OF ENVELOPE GLYCOPROTEIN TRIMERS BY DISULFIDE BONDS INTRODUCED INTO A GP 41 GLYCOPROTEIN ECTODOMAIN

(75) Inventors: Joseph G. Sodroski, Medford, MA (US); Michael Farzan, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 09/164,880

(22) Filed: Oct. 1, 1998

Related U.S. Application Data (60) Provisional application No. 60/060,808, filed on Oct. 3, 1997, and provisional application No. 60/060,813, filed on Oct. 1, 1997.

(51) Int. Cl.[7] .............................................. A61K 39/21
(52) U.S. Cl. ............................... 424/188.1; 424/208.1; 530/350; 435/69.1
(58) Field of Search ...................... 424/188.1, 208.1; 435/69.1; 530/350

(56) References Cited

PUBLICATIONS

F. Barre–Sinoussi et al., *Science,* 229:868–871 (1983).
C. Broder et al., *Proc. Natl. Acad. Sci. USA,* 91:11699–11703 (1994).
D. Chan et al., *Cell,* 89:263–273 (1997).
A. Dalgleish et al., *Nature,* 312:763–767 (1984).
T. Dragic et al., *Nature,* 381:667–673 (1996).
M. Farzan et al., *Journal of Virology,* 72:7620–7625 (1998).
A. Fauci et al., *Annals of Internal Medicine,* 100:92–106 (1984).
P. Earl et al., *Proc. Natl. Acad. Sci. USA,* 87:648–652 (1990).
P. Earl et al., *Journal of Virology,* 65(4):2047–2055 (1991).
Y. Feng et al., *Science,* 272:872–877 (1996).
E. Freed et al., *Proc. Natl. Acad. Sci. USA,* 87:4650–4654 (1990).
R. Gallo et al., *Science,* 224:500–503 (1984).
E. Helseth et al., *Journal of Virology,* 64(5):2416–2420 (1990).
M. Kowalski et al., *Science,* 237:1351–1355 (1987).
D. Klatzman et al., *Nature,* 312:767–769 (1984).
C. Leonard et al., *The Journal of Biological Chemistry,* 265(18):10373–10382 (1990).
J. Moore et al., *Journal of Virology,* 70(3):1863–1872 (1996).
A. Pinter et al., *Journal of Virology,* 63(6):2674–2679 (1989).
M. Schawaller et al., *Virology,* 172:367–369 (1989).
A. Trkola et al., *Nature,* 384:184–187 (1996).
N. Zhou et al., *Biochemistry,* 32:3178–3187 (1993).
International Search Report for PCT/US98/20693, dated Apr. 28, 1999.

*Primary Examiner*—Laurie Scheiner
*Assistant Examiner*—Jeffrey S. Parkin
(74) *Attorney, Agent, or Firm*—Nixon & Peabody LLP (57) ABSTRACT

Biochemical and structural studies of fragments of the ectodomain of the human immunodeficiency virus type 1 (HIV-1) gp41 transmembrane envelope glycoprotein have demonstrated that the molecular contacts between alpha helices allow the formation of a trimeric coiled coil. By introducing cysteine residues into specific locations along these alpha helices, the normally labile HIV-1 gp160 envelope glycoprotein was converted into a stable disulfide-linked oligomer. Although proteolytic cleavage into gp120 and gp41 glycoproteins was largely blocked, the disulfide-linked oligomer was efficiently transported to the cell surface and was recognized by a series of conformationally dependent antibodies. The pattern of hetero-oligomer formation between this construct and an analogous construct lacking portions of the gp120 variable loops and of the gp41 cytoplasmic tail demonstrates that these oligomers are trimers. These results support the relevance of the proposed gp41 structure and intersubunit contacts to the native, complete HIV-1 envelope glycoprotein. Disulfide-mediated stabilization of the labile HIV-1 envelope glycoprotein oligomer, which possesses advantages as an immunogen, will facilitate the development of HIV-1-specific immunological reagents.

5 Claims, 6 Drawing Sheets

FIGURE 1A

```
         560        570        580
          *          *          *
LLRAIEAQQHLLQLTVWGIKQLQARILAVERYL
defgabcdefgabcdefgabcdefgabcdefga
```

STABILIZATION OF ENVELOPE GLYCOPROTEIN TRIMERS BY DISULFIDE BONDS INTRODUCED INTO A GP 41 GLYCOPROTEIN ECTODOMAIN

This application claims the benefit of U.S. Provisional Application Nos. 60/060,808 filing date Oct. 3, 1997 and 60/060,813 filing date Oct. 1, 1997.

Human immunodeficiency virus type 1 (HIV-1) and type 2 (HIV-2) are the etiologic agents of acquired immunodeficiency syndrome (AIDS), which results from the profound depletion of CD4-positive lymphocytes in infected individuals (Barre-Sinoussi, F., Science 1983; Gallo, R. C., et al., Science 1984; Fauci, A. S., et al., Ann Intern Med 1984).

The entry of HIV-1 into target cells is mediated by the viral envelope glycoproteins. The exterior envelope glycoprotein, gp120, and the transmembrane envelope glycoprotein, gp41, are derived from a gp160 precursor (Earl, P. L., et al., J Virol 1984). The gp160 glycoprotein results from the addition of N-linked, high mannose sugar chains to the approximately 845–870 amino acid primary translation product of the env gene in the rough endoplasmic reticulum (ER) [Ibid.]. Oligomers of gp160 form in the endoplasmic reticulum, but the current data do not unambiguously distinguish whether trimers or tetramers constitute this higher-order complex (Earl, P. L., Proc Natl Acad Sci 1987; Pinter, A., et al., J Virol 1989; Schawaller, M., et al., Virology 1989; Lu, M., et al., Nat Struct Biol 1995). Early results studying cell- or virion-associated HIV-1 envelope glycoproteins suggested the formation of dimers, followed by the assembly of dimers into unstable tetramers (Earl, P. L., Proc Natl Acad Sci 1987; Pinter, A., et al., J Virol 1989). This interpretation was supported by the analysis of soluble forms of gp160 lacking a membrane-spanning region (Schawaller, M., et al., Virology 1989). By contrast, studies of peptide fragments of the gp41 ectodomain, which was shown to be necessary of the oligomerization of soluble forms of gp160, revealed a strong tendency for trimer formation (Lu, M., et al., Nat Struct Biol 1995). More recent structural studies of these gp41 peptides have revealed a trimeric coiled coil (Chan, et al. Cell 899: 263–273 (1997); Weissenhorn et al. Nature 384:184–187 (1997)).

HIV-1 infects T lymphocytes, monocytes/macrophage, dendritic cells and, in the central nervous system, microglia (Gartner et al., 1986; Koenig et al., 1986; Pope et al., 1994; Weissman et al., 1995). All of these cells express the CD4 glycoprotein, which serves as the receptor for HIV-1 and HIV-2 (Dalgleish et al., 1984; Klatzman et al., 1984; Maddon et al., 1986). Efficient entry of HIV-1 into target cells is dependent upon binding of the viral exterior envelope glycoprotein, gp120, to the CD4-amino-terminal domain (McDougal et al., 1986; Helseth et al., 1990). After virus binding, the HIV-1 envelope glycoproteins mediate the fusion of viral and host cell membranes to complete the entry process (Kowalski et al., 1987; Stein et al., 1987; Helseth et al., 1990). Membrane fusion directed by HIV-1 envelope glycoproteins expressed on the infected cell surface leads to fusion with uninfected CD4-positive cells, resulting in syncytia (Lifson et al., 1986; Sodroski et al., 1986).

Host cell factors in addition to CD4 are necessary for effective HIV-1 envelope glycoprotein-mediated membrane fusion. Some human and animal cells have been shown to be resistant to HIV-1 infection and syncytium formation even when human CD4 was expressed on the cell surface (Maddon et al., 1986; Ashorn et al., 1990; Chesebro et al., 1990; McKnight et al., 1994). Experiments with somatic cell hybrids suggested the possibility that a positive factor expressed in cells susceptible to syncytium formation could complement he block to fusion in resistant cell types (Clapham et al., 1991; Dragic et al., 1992; Broder et al., 1993). HIV-1 variants exhibiting distinct differences in the ability to fuse with and to enter particular subsets of CD4-positive cells have been identified (Broder and Berger, 1995).

All primary clinical HIV-1 isolates, defined as viruses that have not been passaged on immortalized cell lines, replicate in primary monocytes/macrophages and in primary T lymphocytes. Two groups of primary HIV-1 isolates have been defined, based on replication rate in peripheral blood mononuclear cells (PBMC) and the ability to infect and induce the formation of syncytia in immortalized CD4-positive cell lines (Asjo et al., 1986; Cheng-Mayer et al., 1988; Fenyo et al., 1988; Tersmette et al., 1988).

Most primary HIV-1 viruses that initiate human infection and that persist throughout the course of infection replicate to low levels in PBMC and do not replicate in immortalized T cell lines (Asjo et al., 1986; Schuitemaker et al., 1991; Schuitemaker et al., 1992; Connor et al., 1993, 1994a,b). These viruses are referred to herein as macrophage-tropic primary isolates (sometimes referred to as "M"). In some HIV-1-infected individuals, viruses that replicate to higher levels in PBMC and that can infect and induce the formation of syncytia in immortalized CD4-positive cell lines emerge late in the course of infection (Asjo et al., 1986; Schuitemaker et al., 1992; Connor et al., 1993, 1994a,b). These viruses will be referred to herein as T cell line-tropic primary viruses (sometimes referred to as "T") The T cell line-tropic primary viruses, by virtue of their ability to replicate on some immortalized cell lines, serve as precursors to the laboratory-adapted isolates, which have been extensively passaged on such cell lines. Laboratory adaptation, however, results in a loss of the ability of HIV-1 to replicate in primary monocyte/macrophage cultures (Schuitemaker et al., 1991; Chesebro et al., 1991; Westervelt et al., 1992; Valentin et al., 1994). Thus, while all HIV-1 isolates replicate on primary T lymphocytes, three groups of virus variants can be defined based on the ability to replicate in primary monocyte/macrophages or in immortalized T cell lines: (1) macrophage-tropic primary viruses that cannot infect T cell lines; (2) laboratory-adapted viruses that cannot infect primary monocytes/macrophages; and (3) T cell line-tropic primary viruses that exhibit dual-tropism for these cell types.

Changes in the viral envelope glycoproteins, in particular in the third variable (V3) region of the gp120 exterior envelope glycoprotein, determine tropism-related phenotypes (Cheng-Mayer et al., 1990; O'Brien et al., 1990; Hwang et al., Westervelt et al., 1992; Chesebro et al., 1992; Willey et al., 1994). Amino acid changes in the V3 region (Helseth et al., 1990; Freed et al., 1991; Ivanoff et al., 1991; Bergeron et al., 1992; Grimaila et al., 1992; Page et al., 1992; Travis et al., 1992) and the binding of antibodies to this domain (Putney et al., 1986; Goudsmit et al., 1988; Linsley et al., 1988; Rusche et al., 1988; Skinner et al., Javeherian et al., 1989) have been shown to disrupt a virus entry process other than CD4 binding. The dependence of the phenotype resulting from V3 structural variation on the particular target cell suggested that the V3 region, which contains a surface-exposed, disulfide-linked loop (Leonard et al., 1990; Moore et al., 1994), might act in conjunction with target cell moieties to determine the efficiency of membrane fusion events.

A G protein-coupled seven transmembrane segment receptor, variously called HUMSTR, LCR-1 or LESTR now referred to as CXCR4 (Ferersppiel et al., 1993; Jazin et al., 1993; Loetscher et al., 1994) has been shown to allow a range of non-human, CD4-expressing cells to support infection and cell fusion mediated by laboratory-adapted HIV-1 envelope glycoproteins (Feng et al., 1996). Antibodies to HUMSTR blocked cell fusion and infection by laboratory-adapted HIV-1 isolates but not by macrophage-tropic primary viruses (Feng et al., 1996). While its natural ligand is currently unknown, HUMSTSR exhibits sequence similarity to the receptor for interleukin-8, an alpha (CXC) chemokine) (Probst et al., 1992). Other G-protein-coupled seven transmembrane segment receptors such as CCR5, CCR3 and CCR2 have been shown to assist cellular entry of other HIV-1 isolates. It is believed that the cellular entry occurs as a result of the interaction of gp120, CD4 and the chemokine receptor.

These discoveries emphasize the significant role env plays in viral entry. And they further illustrate the importance of env as a target in inhibiting the spread of infection. However, attempts at targeting env have not been as successful as hoped. For example, early attempts were made to develop vaccines based upon using a subunit approach, which focuses on using less antigens then present in the entire virus, because of the significant health concerns raised in using attenuated or inactivated whole HIV because of the severity of HIV infection. A key subunit vaccine target was the envelope glycoprotein. However, these attempts at developing a subunit vaccine using the env were not successful. Even generating antibodies to env that can neutralize a wide range of HIV strains initially presented many difficulties. While considerable improvement has occurred in understanding how to generate antibodies to env, e.g. gp120 antibodies; such as by using gp120 conformational polypeptides where portions of the variable regions have been eleted, further improvements would be useful.

SUMMARY OF THE INVENTION

We have discovered DNA sequences encoding env, where we can introduce sequences encoding cysteine residues in a portion encoding the gp 41 transmembrane envelope glycoprotein. These sequences will express proteins that can stably oligomerize in a conformation approaching the native virus. The introduction of these residues creates the molecular contacts between alpha helices that stabilize the trimeric coiled coil, which is responsible for the oligomerization of the HIV-1 envelope glycoprotein. These cysteine residues are introduced in specific locations along these alpha helices. One preferred location is at the residues adjacent to the d and e positions of the coiled coil helix such as positions 576 and 577 of HIV-1. It is also preferred that an adjoining amino acid residue be substituted to provide greater flexibility in the protein backbone; one example is the substitution of a gly at the f position such as 578 of HIV-1. As a result of these changes, the normally labile HIV-1 gp160 envelope glycoprotein was converted into a stable disulfide-linked oligomer that was expressed on the cell surface and had a conformation approaching that of the native glycoprotein as demonstrated by its ability to be recognized by a series of conformationally dependent antibodies. The pattern of hetero-oligomer formation between this construct and an analogous construct lacking portions of the gp120 variable loops and of the gp41 cytoplasmic tail demonstrates that these oligomers are trimers. The stabilized oligomer can be used to generate a range of antibodies that recognize and interact with a diverse range of HIV strains. The DNA sequence can also be used as a subunit vaccine.

BRIEF DESCRIPTION OF THE DRAWINGS

FIGS. 1A and 1B show coiled coil regions from env.

FIG. 1A shows models of coiled coils. The top view of a segment of model dimeric, trimeric and tetrameric coiled coils is shown. The Cα, Cβ and Cγ atoms for residues for which the interhelical Cα—Cα and Cβ—Cβ distances are at a minimum are depicted. Typical interhelical distances for the dimer (O'Shea, E., et al., *Science* 1991) at the d position (shown in dark) of the heptad repeat are 6.1 angstroms for the Cα—Cα and 3.7 angstroms for the Cβ—Cβ distance. The typical Cα—Cα and Cβ—Cβ distance from the d (dark) to e (white) positions in the trimer are 7.2 and 7.1 angstroms, respectively (Harbury, P. B., et al., *Nature* 1994). In the tetrameric coiled coil, the a position (dark) is closest to the g position (white) of an adjacent helix, with a Cα—Cα distance of 6.7 angstroms and a Cβ—Cβ distance of 4.2 angstroms (Harbury, P. b., et al., *Science* 1993). Ideal distances for the introduction of a disulfide are Cα—Cα<6,5 angstroms and Cβ—Cβ<4.5 angstroms (Reiter, Y., et al., *Protein Eng* 1988; Sowdhamini, R., et al., *Protein Eng* 1989).

FIG. 1B shows a portion of the gp41 protein containing the amino acid sequence of the coiled coil region of the gp41 (SEQ ID NO: 11), indicating residue number and the position along the heptad repeat of the coil.

FIG. 2 shows immunoprecipitation of HIV-1 envelope glycoprotein variants. Plasmids encoding the wild-type HIV-1 envelope glycoproteins and three of the mutant envelope glycoproteins described in Table 1 were transfected into COS-1 cells. Cell lysates were immunoprecipitated with the anti-gp41 antibody D61, and the precipitates were boiled in 2% β-mercaptoethanol for 3 minutes prior to analysis on an 8% SDS-polyacrylamide gel.

FIG. 3 shows analysis of wild-type and LQA/CCG envelope glycoproteins. Lysates were immunoprecipitated with the anti-gp41 antibody D61 and boiled in either 2% or 5% β-mercaptoethanol for 3 or 10 minutes, as indicated, prior to analysis on an 8% polyacrylamide gel.

FIG. 4 shows precipitation of LQA/CCG and ΔLQA/CCG envelope glycoproteins with antibodies. Lysates containing the LQA/CCG and the ΔLQA/ CCG envelope glycoproteins were precipitated with HIV-1-infected patient sera (PS1, PS2), the F105 antibody, the 17b antibody in the presence or absence of soluble CD4, the C11 antibody, or the G3-519 antibody. The A32 antibody and the anti-gp41 antibodies D61, T3 and T4 all recognized both monomeric and higher order forms of LQA/CCG and ΔLQA/CCG envelope glycoproteins (data not shown). The 110.4 antibody, directed against the third variable loop of gp120, recognized the LQA/CCG glycoprotein (data not shown and FIG. 5, lane 5).

FIG. 5 shows formation of hetero-oligomers between LQA/CCG and ΔLQA/CCG envelope glycoproteins. Serum from an HIV-1 infected individual was used to precipitate lysates of 293T cells transfected with plasmids encoding LQA/CCG (lane 1) and ΔLQA/CCG (lane 4) envelope glycoproteins. In lane 2, plasmids expressing the LQA/CCG and ΔLQA/CCG envelope glycoproteins were transfected at a 2:1 ratio, while in lane 3, the LQA/CCG- and ΔLQA/CCG-expressing plasmids were transfected in equal amounts. In lane 5, the same cell lysates as those used for the experiment in lane 3 were used for precipitation by the anti-V3 loop antibody 110.4.

FIG. 6 shows potential sites for disulfide cross-linking of the HIV-1 envelope glycoprotein trimer. The structure of the gp41 ectodomain peptides assembled into the helical coiled coil is shown. The sites of intersubunit interactions at the d and e positions of the coiled coil are shaded, as is the site of the LQA/CCG mutant (dark shading) shown to allow cross-linking of gp160 trimers. Both cys-cys and cys-cys-gly substitutions can be made at the indicated locations along the coiled coil. Substitutions that result in disulfide bridges and trimer stabilization can also be used in combination.

DETAILED DESCRIPTION OF THE INVENTION

We have now discovered an improved immunogenic gp120-gp 41 oligomer, sometimes referred to as gp160 and DNA sequences encoding them. This oligomer is stabilized by the creation of cysteine-SH-cysteine bonds. Moreover, by appropriate placement of the cysteine residue in the gp 41 portion, the resulting oligomer forms spikes similar to that seen in the native wild type virus. Consequently, antibodies generated by these polypeptides are more likely to recognize and interact with native virus.

The gp160 glycoprotein is the precursor for gp 120 and gp 41. Following oligomerization of the precursor the gp160 glycoprotein is transported to the Golgi apparatus where cleavage by a cellular protease generates the gp120 and gp41 glycoproteins, which remain associated through non-covalent interactions (Earl, P. L., et al., *J Virol* 1991; Kowalski, M., et al., *Science* 1987). In mammalian host cells, addition of complex sugars to selected, preferably surface-exposed, carbohydrate side chains of the envelope glycoproteins occurs in the Golgi apparatus (Leonard, C. K., et al, *J Biol Chem* 1990).

The mature envelope glycoprotein complex is incorporated into virions, where it mediates virus entry into the host cell. The gp120 exterior envelope glycoprotein binds the CD4 glycoprotein, which serves as a receptor for the virus (Klatzmann, D., et al., *Nature* 1984, Dalgleish, A. G., et al, *Nature* 1984). Because gp120 is external as discussed above it was proposed as a natural target for trying to develop an immune response to prevent viral entry. However, in part due to the numerous variable regions which can mutate rapidly, the wild type gp 120 has not proven to be a successful target. An approach to using a modified gp 120 polypeptide wherein at least portions of the variable region have been removed, while the overall 3-dimensional conformation is retained [Sodroski, et al, 39813 which is incorporated herein by reference] has avoided some of these problems.

The importance of the envelope glycoprotein has been underscored by recent discoveries. The binding of gp 120 to CD4 is followed by interaction of the gp120-CD4 complex with one of the chemokine receptors, which are seven-transmembrane G protein-coupled receptors (Feng, Y., et al., *Science* 1996; Choe, H., et al., *Cell* 1996; Doranze, et al., *Cell* 1996; Dragic, et al., *Nature* 1996; Alkhatib, G., et al., *Science* 1996). The chemokine receptor interaction is believed to bring the viral envelope glycoprotein complex nearer to the target cell membrane and to trigger additional conformational changes in the envelope glycoproteins (Wu, L., et al., *Nature* 1996; Trkola, A., et al., *Nature* 1996). These changes are proposed to result in the interaction of the gp41 glycoprotein with the target cell membrane, culminating in fusion of this membrane with the viral membrane. Such a model is consistent with mutagenic analysis. Amino acid changes in the hydrophobic gp41 amino terminus (the "fusion peptide"), in the amino-terminal half of the ectodomain, or in the transmembrane region all result in fusion-defective envelope glycoproteins (Kowalski, M., *Science* 1987; Freed, E. O., *Proc Natl Acad Sci* 1990; Cao, J., *J Virol* 1993). All these factors confirm the importance of the envelope glycoprotein. However, in nature an oligomeric form is seen. Thus, being able to prepare a stable oligomer containing the gp 120 portion is extremely important. Yet, the stable oligomer must approximate the conformation of the oligomer formed naturally. This has proven difficult. First, the HIV-1 envelope glycoprotein oligomer is naturally labile, disassociating into individual subunits readily. Second, the introduction of cysteine residues in inappropriate positions can result in non-native structures. Since these molecules are folded differently than the native HIV-1 envelope glycoproteins, their utility in raising antibodies that recognize and neutralize the viral envelope spike is limited. We have discovered that there are only a limited number of positions in the gp 41 portion that can be used to create a stable oligomer that approximates the native conformation.

Soluble forms of HIV-1 envelope glycoprotein oligomers should have advantages over monomeric gp120 preparations as immunogens, since the former are more likely to mimic the native envelope glycoprotein spike on virions (Broder, C. C., et al., *Proc Natl Acad Sci USA* 1994). Unfortunately, due to the lability of HIV-1 envelope glycoprotein, the preparation of high-quality stable oligomers that maintain high-order states has been difficult. We have found that preparation of a DNA sequence encoding complex having selective introduction of cysteine residues in the gp41 ectodomain helices results in disulfide bonds, between the expressed monomers resulting in stable envelope glycoprotein oligomers having a conformation approximating the native as demonstrated by the binding of antibodies to native of the oligomer to these constructs. Present in an N-terminal gp41 alpha helix is a heptad repeat of hydrophobic residues at the first ('a') and fourth position ('d'), which is the hallmark of a coiled coil (O'Shea, et al., *Science* 1991). Coiled coils are believed to play a central role in influenza virus entry mediated by the hemagglutinin molecule, where the extension of a trimeric coiled coil in the transmembrane $HA_2$ subunit is thought to mark the transition to a fusogenic conformation of this protein (Carr, C. M., et al., *Cell* 1993; Bullogh, P. A., *Nature* 1994). Recently, a crystal structure of an HIV-1 gp41 ectodomain fragment has been obtained, confirming the existence of a trimeric coiled coil that is bound and stabilized by three monomers of a C-terminal helix (Chan, D. C., *Cell* 1997). It was not clear from this data if this is the form used by the complex of gp 120-gp41 because the HIV-1 gp41 glycoprotein is thought to undergo conformational changes from its conformation in the gp160 precursor. Consequently, whether the crystallographic structure obtained for the gp41 ectodomain fragment corresponds to that found in the gp160 envelope glycoprotein precursor or represents a fusion-competent conformation was uncertain. The results we have obtained demonstrate the relevance of the available gp41 structures to the complete HIV-1 envelope gp 160 (gp 20–gp41) and imply that at least some of the molecular contacts observed are present before the induction of a fusogenic conformation.

By using DNA sequences encoding gp160 and/or gp41–gp120 proteins and by selective introduction of cysteines at specific locations in the HIV-1 gp41 coiled coil we can stabilize dimeric and trimeric forms of a conformational gp160 polypeptide such as based upon a processing-defective gp160 glycoprotein. This glycoprotein was expressed efficiently on the cell surface and was precipitated by antibodies that recognize conformation-dependent gp120 epitopes (Moore, J. P., et al., *J Virol* 1996; Thali, M., et al.,

*J Virol* 1993) but was gp 160 processing defective. Thus, the impaired processing not appear to result from inefficient folding or transport along the secretory pathway. Although not wishing to be bound by theory we believe the processing defect could reflect a subtle conformational alteration in the envelope glycoprotein region recognized by the cellular protease, or could suggest that a degree of flexibility at the gp 120/gp41 cleavage site is necessary for efficient processing and is not present in the LQA/CCG mutant.

Traditional approaches at generating antibodies to env have typically focused on the gp120 polypeptide. However, we found that creating a fusion protein containing a gp120 portion, preferably a modified gp 120 portion, and a modified gp 41 portion permits the creation of stable oligomers.

As will be discussed in detail below the preferred modified gp 120 portion is a gp 120 protein that has been modified to have variable loops or portions thereof.

The HIV-1 envelope glycoprotein oligomer may be stabilized through intersubunit disulfide bonds. One preferred structure has cysteine residues introduced at residues adjacent to the d and e positions of the coiled coil helix in gp 41. See FIG. 1B for the amino acid and a nucleotide sequence of this region. These positions correspond to 576 and 577 of HIV-1. These residues are highly conserved among HIV-1 and HIV-2 strains, indicating that the approach is applicable to both HIV-1 and HIV-2. These positions correspond to 576 and 577 of the HXBc2 isolate of HIV-1. The numbering varies slightly for different HIV-1 isolates, although the sequence in this region of the gp41 coiled coil is largely conserved. Therefore, the equivalently positioned residues are easily identified in other HIV-1 and, in fact, in HIV-2 envelope glycoproteins as well.

Figure 6:
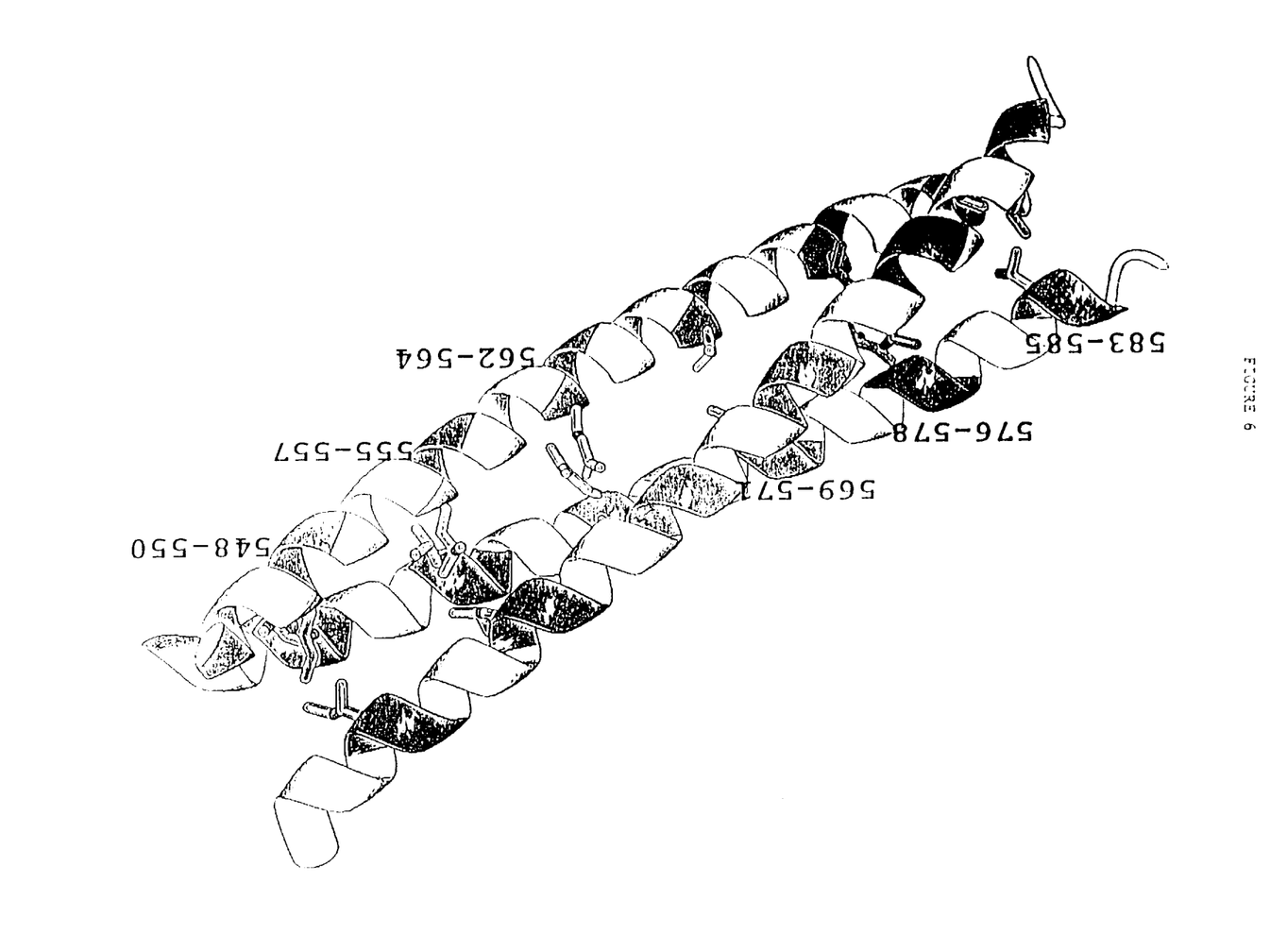

Other sites along the gp41 coiled coil could also be used for the introduction of cysteines (See FIG. 6). These sites are numbered 555/556, 562/563, 569/570, and 583/584 in the HXBc2 HIV-1 sequence. Analogous to the glycine substitution at position 578, glycines could be introduced adjacent to the introduced cysteines, at positions 557, 564, 571 and 584, respectively.

In order to maintain the overall conformation it is desirable to substitute an adjoining amino acid residue with one that provides flexibility in turning. Preferably, the residue is Gly. For example, substituting gly for ala at position f of the helix in the above example of 576/577 corresponds to position 578. These monomers are useful in producing stable trimers for structural or vaccine purposes, where the lability of these higher-order forms has been problematic. Disulfide crosslinking of the HIV-1 envelope glycoprotein trimer stabilizes otherwise labile neutralization epitopes specific for the oligomer and the form can mask biologically irrelevant epitopes that are exposed on the gp 120 or gp160 monomer but buried on the functional oligomer, and lengthen the half-life of the intact vaccine construct in the body. With the availability of a crystallographic model of the gp41 exterior domain, the disulfide crosslinking strategy described herein can be used with other elements of the gp 41 coiled coil based upon our teaching (See FIG. 6).

Dimers as well as trimers of the mutant may be stabilized by the formation of disulfide bonds. The dimer form of the mutant was less abundant than the trimer and was more sensitive to a disruption by boiling (data not shown). Stable dimers could represent intermediates in the assembly or disassembly of the trimer. Alternatively, the dimer could result from the formation of an alternative disulfide bond between the cysteines in the d positions, excluding the possibility of forming the three d-e disulfide bonds presumably present in the trimer. However, we believe the dimer is an artifact.

The oligomer complexes can be used to generate a range of antibodies to gp120 and gp41. For example, antibodies that affect the interaction with the binding site can be directly screened for example using a direct binding assay. For example, one can label, e.g. radioactive or fluorescent, a gp120 protein or derivative and add soluble CD4. There are various soluble CD4s known in the art including a two-domain (D1D2 sCD4) and a four-domain version. The labeled gp120, or derivative, e.g., a conformationally intact deletion mutant such as one lacking portions of the variable loops (e.g. V1/V2) and in some instances constant regions and soluble CD4 can be added to medium containing a cell line expressing a chemokine receptor that the antibody will block binding to. In this example, the derivative will blocking binding to CCR5. Alternatively, when using a derivative from a T cell tropic gp120 one would use a cell line that expresses CXCR4. Binding can then be directly measured. The antibody of interest can be added before or after the addition of the labeled gp120 or derivative and the effect of the antibody on binding can be determined by comparing the degree of binding in that situation against a base line standard with that gp120 or derivative, not in the presence of the antibody.

A preferred assay uses the labeled gp120, or derivative portion, for example a gp120 protein derived from an M-tropic strain such as JR-FL, iodinated using for instance solid phase lactoperoxidase (in one example having a specific activity of 20 $\mu Ci/\mu g$). The cell line containing the chemokine receptor in this example would be a CCR5 cell line, e.g. L1.2 or membranes thereof. Soluble CD4 would be present.

In one embodiment, the conformational gp 120 portion should contain a sufficient number of amino acid residues to define the binding site of the gp120 to the chemokine receptor (e.g. typically from the V3 loop) and a sufficient number of amino acids to maintain the conformation of the peptide in a conformation that approximates that of wild-type gp120 bound to soluble CD4 with respect to the chemokine receptor binding site. In other embodiments the V3 loop can be removed to remove masking amino acid residues. In order to maintain the conformation of the polypeptide one can insert linker residues that permit potential turns in the polypeptides structure. For example, amino acid residues such as Gly, Pro and Ala. Gly is preferred. Preferably, the linker residue is as small as necessary to maintain the overall configuration. It should typically be smaller than the number of amino acids in the variable region being deleted. Preferably, the linker is 8 amino acid residues or less, more preferably 7 amino acid residues or less. Even more preferably, the linker sequence is 4 amino acid residues or less. In one preferred embodiment the linker sequence is one residue. Preferably, the linker residue is Gly.

In one preferred embodiment, the gp120 portion also contains a CD4 binding site (e.g. from the C3 region residues 368 and 370, and from the C4 region residues 427 and 457). The chemokine binding site is a discontinuous binding site that includes portions of the C2, C3, C4 and V3 regions. By deletion of non-essential portions of the gp120 polypeptide—such as deletions of portions of non-essential variable regions (e.g. V1/V2) or portions in the constant regions (e.g. C1, C5) one can increase exposure of the CD4 binding site. Another embodiment is directed to a gp120 portion containing a chemokine binding site. Similarly, by deleting the non-essential portions of the protein one can increase exposure of the chemokine binding site. The increased exposure enhances the ability to generate an antibody to the CD4 receptor or chemokine receptor, thereby inhibiting viral entry. Removal of these regions is done while requiring the derivative to retain an overall conformation approximating that of the wild-type protein with respect to the native gp120 binding region, e.g. the chemokine binding region when complexed to CD4. In addition, one can remove glycosylation sites that are disposable for proper folding. Maintaining conformation can be accomplished by using the above-described linker residues that permit potential turns in the structure of the gp120 derivative to maintain the overall three-dimensional structure. Preferred amino acid residues that can be used as linker include Gly and Pro. Other amino acids can also be used as part of the linker, e.g. Ala. Examples on how to prepare such peptides are described more fully in Wyatt, R., et al. *J. of Virol.* 69:5723–5733 (1995); Thali, M., et al., *J. of Virol.* 67:3978–3988 (1993); and U.S. application Ser. No. 07/858,165 filed Mar. 26, 1992 which are incorporated herein by reference. See for example Wyatt which teaches how to prepare V1/V2 deletions that retain the stem portion of the loop.

In one embodiment the gp120 derivative is designed to be permanently attached at the CD4 binding site to sufficient domains of CD4 to create a conformation of the chemokine binding site approximating that of the native gp120 CD4 complex.

An alternative gp120 derivative is one wherein the linkers used result in a conformation for the derivative so that the discontinuous binding site with the chemokine receptor approximates the conformation of the discontinuous binding site for the chemokine receptor in the wild-type gp120/CD4 complex. These derivatives can readily be made by the person of ordinary skill in the art based upon the above described methodologies and screened in the assays shown herein to ensure that proper binding is obtained.

The gp120 polypeptide portion is bound to at least a portion of gp41 polypeptide, namely the coiled coil. Some of these derivatives will lack the gp41 transmembrane region and will therefore be made as secreted, soluble oligomers. For example, gp41 portions lacking the transmembrane region but retaining the cytoplasmic region, others truncated beginning with the transmembrane region, and therefore also lacking the cytoplasmic region. In an alternative embodiment, one can substitute amino acid residues in the transmembrane region which results in anchoring the protein with other amino acid residues. Preferably, those amino acids although being residues that do not bind to the membrane, would be selected to have minimal conformational effect on the polypeptides. These amino acids can readily be selected by the skilled artisan based upon known knowledge in view of the present disclosure. This can be done by standard means using known techniques such as sets directed mulogenesis. The gp41 polypeptide contains the indicated cysteine residues, which result in the formation of the SH bonds between the monomers thereby stabilizing the complex as a trimer having spikes similar to that found in the wild type. These immunogenic oligomers can be used to generate an immune reaction in a host by standard means. For example one can administer the trimeric protein in adjuvant. In another approach, a DNA sequence encoding the gp120–gp41 complex can be administered by standard techniques. The approach of administering the protein is presently preferred.

The protein is preferably administered with an adjuvant. Adjuvants are well known in the art and include aluminum hydroxide, Ribi adjuvant, etc. The administered protein is typically an isolated and purified protein. The protein is preferably purified to at least 95% purity, more preferably at least 98% pure, and still more preferably at least 99% pure. Methods of purification while retaining the conformation of the protein are known in the art. The purified protein is preferably present in a pharmaceutical composition with a pharmaceutically acceptable carrier or diluent present.

DNA sequences encoding these proteins can readily be made. For example, one can use the native gp 160 of any of a range of HIV-1 strains which are well known in the art and can be modified by known techniques such to deleted the undesired regions such as variable loops and to insert desired coding sequences such as cysteines and linker segments. In addition to DNA sequences based upon existing strains, the codons for the various amino acid residues are known and one can readily prepare alternative coding sequences by standard techniques.

DNA sequences can be used in a range of animals to express the monomer, which then forms into the trimer and generates an immune reaction.

DNA sequences can be administer to a host animal by numerous methods including vectors such as viral vectors, naked DNA, adjuvant assisted DNA catheters, gene gun, liposomes, etc. In one preferred embodiment the DNA sequence is administered to a human host as either a prophylactic or therapeutic treatment to stimulate an immune response, most preferably as a prophylactic. One can administer cocktails containing multiple DNA sequences encoding a range of HIV env strains.

Vectors include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include herpes virus vectors such as a herpes simplex I virus (HSV) vector [Geller, A. L et al. *J. Neurochem* 64: 487 (1995); Lim, F. et al., in *DNA Cloning: Mammalian Systems*, D. Glover, Ed. (*Oxford Univ. Press, Oxford England*) (1995); Geller, A. I. et al., *Proc Natl. Acad. Sci. U.S.A.* 90: 7603 (1993); Geller, A. I., et al., *Proc Natl. Acad. Sci USA* 87: 1149 (1990)], adenovirus vectors [LeGal LaSalle et al., *Science* 259: 988 (1993); Davidson, et al., *Nat. Genet* 3: 219 (1993); Yang, et al., *J. Virol.* 69: 2004 (1995)] and adeno-associated virus vectors [Kaplitt, M. G., et al., *Nat. Genet.* 8:148 (1994)].

The DNA sequence would be operably linked to a promoter that would permit expression in the host cell. Such promoters are well known in the art and can readily be selected. Stabilized forms of these complexes can readily be made, for example, by conjugates such as a poly(alkylene oxide) conjugate. The conjugate is preferably formed by covalently bonding the hydroxyl terminals of the poly (alkylene oxide) and a free amino group in the gp120 portion that will not affect the conformation of the discontinuous binding site. Other art recognized methods of conjugating these materials include amide or ester linkages. Covalent linkage as well as non-covalent conjugation such as lipophilic or hydrophilic interactions can be used.

The conjugate can be comprised of non-antigenic polymeric substances such as dextran, polyvinyl pyrrolidones, polysaccharides, starches, polyvinyl alcohols, polyacryl amides or other similar substantially non-immunogenic polymers. Polyethylene glycol(PEG) is preferred. Other poly(alkylenes oxides) include monomethoxy-polyethylene glycol polypropylene glycol, block copolymers of polyethylene glycol, and polypropylene glycol and the like. The polymers can also be distally capped with C1–4 alkyls instead of monomethoxy groups. The poly(alkylene oxides) used must be soluble in liquid at room temperature. Thus, they preferably have a molecular weight from about 200 to about 20,000 daltons, more preferably about 2,000 to about 10,000 and still more preferably about 5,000.

One can administer these stabilized compounds to individuals by a variety of means. For example, these antibodies can be included in vaginal foams or gels that are used as preventives to avoid infection and applied before people have sexual contact.

The peptides or antibodies when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 $\mu$g/kg a day, more preferably 1 to 10,000 $\mu$g/kg.

Routes of administration include oral, parenteral, rectal, intravaginal, topical, nasal, ophthalmic, direct injection, etc.

Changes in the viral envelope glycoproteins, in particular in the third variable (V3) region of the gp120 exterior envelope glycoprotein, determine tropism-related phenotypes (Cheng-Mayer et al., 1990; O'Brien et al., 1990; Hwang et al., Westervelt et al., 1992; Chesebro et al., 1992; Willey et al., 1994). Amino acid changes in the V3 region (Helseth et al., 1990; Freed et al., 1991; Ivanoff et al., 1991; Bergeron et al., 1992; Grimaila et al., 1992; Page et al., 1992; Travis et al., 1992) and the binding of antibodies to this domain (Putney et al., 1986; Goudsmit et al., 1988; Linsley et al., 1988; Rusche et al., 1988; Skinner et al., Javeherian et al., 1989) have been shown to disrupt a virus entry process other than CD4 binding. Accordingly, one can create derivatives and change the phenotype for a particular receptor by substituting V3 loops.

One can inhibit infection by directly blocking receptor binding. This can be accomplished by a range of different approaches. For example, antibodies. One preferred approach is the use of antibodies to the binding site for these chemokine receptors. Antibodies to these receptors can be prepared by standard means using the stable immunogenic oligomers. For example, one can use single chain antibodies to target these binding sites. As used herein the inhibition of HIV infection means that as compared to a control situation infection is reduced, inhibited or prevented. Infection is preferably at least 20% less, more preferably at least 40% less, even more preferably at least 50% less, still more preferably at least 75% less, even more preferably at least 80% less, and yet more preferably at least 90% less than the control.

One preferred use of the antibodies is to minimize the risk of HIV transmission. These antibodies can be included in ointments, foams, creams that can be used during sex. For example, they can be administered preferably prior to or just after sexual contact such as intercourse. One preferred composition would be a vaginal foam containing one of the antibodies. Another use would be in systemic administration to block HIV-1 replication in the blood and tissues. The antibodies could also be administered in combination with other HIV treatments.

Pharmaceutic Compositions

An exemplary pharmaceutical composition is a therapeutically effective amount of a the oligomer, antibody etc. that for examples affects the ability of the receptor to facilitate HIV infection or for the DNA sequence or the oligomer that can induce an immune reaction, thereby acting as a prophylactic immunogen, optionally included in a pharmaceutically-acceptable and compatible carrier. The term "pharmaceutically-acceptable and compatible carrier" as used herein, and described more fully below, includes (i) one or more compatible solid or liquid filler diluents or encapsulating substances that are suitable for administration to a human or other animal, and/or (ii) a system, such as a retroviral vector, capable of delivering the molecule to a target cell. In the present invention, the term "carrier" thus denotes an organic or inorganic ingredient, natural or synthetic, with which the molecules of the invention are combined to facilitate application. The term "therapeutically-effective amount" is that amount of the present pharmaceutical compositions which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic internal after the initial administration. Various concentrations may be used in preparing compositions incorporating the same ingredient to provide for variations in the age of the patient to be treated, the severity of the condition, the duration of the treatment and the mode of administration.

The term "compatible", as used herein, means that the components of the pharmaceutical compositions are capable of being commingled with a small molecule, nucleic acid and/or polypeptides of the present invention, and with each other, in a manner such that does not substantially impair the desired pharmaceutical efficacy.

Dose of the pharmaceutical compositions of the invention will vary depending on the subject and upon particular route of administration used. Dosages can range from 0.1 to 100,000 $\mu$g/kg per day, more preferably 1 to 10,000 $\mu$g/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at 5 months after second dose. See Product Information, *Physician's Desk Reference*, Merck Sharp & Dohme (1990), at 1442–43. (e.g., Hepatitis B Vaccine-type protocol); (ii) Recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See Product Information, Physician's Desk Reference, Merck Sharp & Dohme (1990), at 879 (e.g., Diptheria, Tetanus and Pertussis-type vaccine protocols). Desired time intervals for delivery of multiple doses of a particular composition can be determined by one of ordinary skill in the art employing no more than routine experimentation.

The antibodies, DNA sequences or oligomers of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

The compositions include those suitable for oral, rectal, intravaginal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. Methods typically include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Antibodies

The term "antibodies" is meant to include monoclonal antibodies, polyclonal antibodies and antibodies prepared by recombinant nucleic acid techniques that are selectively reactive with polypeptides encoded by eukaryotic nucleotide sequences of the present invention. The term "selectively reactive" refers to those antibodies that react with one or more antigenic determinants on e.g. gp120 and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes, as well as to block bindiner interactions.

For example, cDNA clone encoding a gp120-gp41 complex of the present invention may be expressed in a host using standard techniques (see above; see Sambrook et al., Molecular Cloning; A Laboratory Manual, Cold Spring Harbor Press, Cold Spring Harbor, N.Y.: 1989) such that 5–20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Preferably, one would design a stable cell could expressing high levels of the proteins which be selected and used to generate antibodies For example, mice can be immunized twice intraperitoneally with approximately 50 micrograms of protein immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of polypeptides encoded by a eukaryotic nucleotide sequence of the present invention may be analyzed in order to identify desired portions of amino acid sequence which may be associated with receptor binding. For example, polypeptide sequences may be subjected to computer analysis to identify such sites.

For preparation of monoclonal antibodies directed toward polypeptides encoded by a eukaryotic nucleotide sequence of the invention, any technique that provides for the production of antibody molecules by continuous cell lines may be used. For example, the hybridoma technique originally developed by Kohler and Milstein (Nature, 256: 495–497, 1973), as well as the tribma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

The monoclonal antibodies may be human monoclonal antibodies or chimeric human-mouse (or other species)

monoclonal antibodies. The present invention provides for antibody molecules as well as fragments of such antibody molecules.

Those of ordinary skill in the art will recognize that a large variety of possible moieties can be coupled to the resultant antibodies or to other molecules of the invention. See, for example, "Conjugate Vaccines", Contributions to Microbiology and Immunology, J. M. Cruse and R. E. Lewis, Jr (eds), Carger Press, N.Y., (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, "Specific killing of lymphocytes that cause experimental Autoimmune Myasthenia Gravis by toxin-acetylcholine receptor conjugates." Jour. Immun. 133:1335–2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185–216; and Vitetta et al., supra).

Preferred linkers are described in the literature. See, for example, Ramakrishnan, S. et al., Cancer Res. 44:201–208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)propianamidel]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Antibodies of the present invention can be detected by appropriate assays, such as the direct binding assay discussed earlier and by other conventional types of immunoassays. For example, a sandwich assay can be performed in which the receptor or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

The following Examples serve to illustrate the present invention, and are not intended to limit the invention in any manner.

MATERIALS AND METHODS

Cells and Monoclonal Antibodies

COS-1, HeLa and 293T cells were maintained in DME supplemented with 10 percent fetal bovine serum. The monoclonal antibodies F105, 17b, C11, G3-519, 212A, A32, #45 and 110.4 were obtained from the sources described in Moor, et al, 1993. The monoclonal antibodies D61, T2, T3, and T4 were generously provided by Drs. Patricia Earl and Robert Doms (Broder, C. C., et al., *Proc natl Acad Sci USA* 1994). Sera were obtained from HIV-1 infected individuals.

Creation of Plasmids Expressing Mutant Envelope Glycoproteins

All mutant HIV-1 envelope glycoproteins were expressed from the pSVIIIenv plasmid, which has been previously described (Helseth, E., *J Virol* 1990). Site-directed mutagenesis using a single-stranded template was used to create plasmids expressing the mutant envelope glycoproteins, as described (Cao, J., *J Virol* 1993). The following primers were used:

CAGCATCTGTTGCAGCTGTGCT-TGGGGCACAAGCAG (569 T/C mutant) (SEQ ID. NO.:1),

CAAGCAAGAATCCTAGCCTGTGAAAGG-TACCTAAAGGAT (583 V/C mutant) (SEQ ID. NO.: 2),

AGAATCCTAGCTGTGGAGCGCTGCTG-TAAGGATCAACAGCTC (586/7 YL/CC mutant) (SEQ. ID. NO.: 3), GCTATTGAGGCGCAACAGGGTTGCTGCG-GTCTCACAGTCTGGGGCATC (564/5/6/7 HLLQ/GCCG mutant)(SEQ. ID. NO.: 4), ATTGAGGCGCAACAGCACCTGCTGCAAG-GCTGCTGCTGGGGCATCAAGCAGCTC (568/69/70 LTV/GCC mutant) (SEQ. ID. NO.: 5), TTGCAACTCACAGTCGGGGTGCTGTGGC-CAGCTCCAAGCAAGAATC (571/2/3/4 WGIK/GCCG mutant) (SEQ. ID. NO.: 6),
GTCTGGGGCATCAAGCAGTGCTGCGGAA-GAATTCTAGCTGTGGAAAGA (576/7/9 LQA/CCG mutant) (SEQ. ID. NO.: 7),
ATCAAGCAGCTCCAAGGATGCTGCG-GCGCCGTGGAAAGATACCTAAAG (578/79/80/81 ARIL/GCCG mutant) (SEQ. ID. NO.: 8),
CAAGCAAGAATCCTAGGTTGTTGTA-GATATCTAAAGGATCCACAGCTC (582/3/4 AVE/GCC mutant) (SEQ. ID. NO.: 9),
AGAATCCTAGCTGTGGAAGGATGCTGCG-GTGATCAACAGCTCGGGATT (583/4/5 VER/CCG mutant) (SEQ. ID. NO.: 10).

The ΔV1/V2/V3 (tail-) 576/7/8 LQA/CCG construct was made by introducing the 576/7/8 LQA/CCG mutation into a previously described HIV-1 envelope glycoprotein construct (Wyatt, R., et al., *J Virol* 1995), in which residues 128–194 and 298–303 were replaced by glycine-alanine-glycine connectors, and a stop codon was introduced to produce an envelope glycoprotein truncated after residue 712 (Mammano, F., *J Virol* 1995).

Transfections, Metabolic Labeling and Analysis of Envelope Glycoproteins

Cells were transfected by the calcium phosphate method, using 25 µg of he pSVIIIenv plasmid expressing wild-type or mutant envelope glycoproteins, as described (Cao, J., *J Virol* 1993). Transfected cells were labeled with $^{35}$-Scysteine and used for analysis of envelope glycoproteins. For studying expression and the presence of higher-order forms of the envelope glycoproteins, labeled cells were lysed in NP40 buffer (0.5% NP40, 0.5 M NaCl, 10 mM Tris, pH 7.5) and used for immunoprecipitation by serum from an HIV-1 infected individual. Precipitates-were boiled in sample buffer containing from 0 to 5% β-mercaptoethanol for 3 to 10 minutes prior to analysis on 7 or 10% SDS-polyacrylamide gels. In some experiments, 10 mM iodoacetamide was included in lysis and sample buffers and in these cases, no β-mercaptoethanol was added to the sample buffer prior to analysis on SDS-polyacrylamide gels. For analysis of the conformation of the mutant envelope glycoproteins, radiolabeled cell lysates in NP40 buffer were precipitated with the antibodies described above. Precipitates were analyzed on an 8 percent SDS-polyacrylamide gel after boiling in sample buffer containing 0.4% β-mercaptoethanol.

Cell surface expression of the envelope glycoproteins was assessed by incubating labeled, transfected 293T cells with 0.5 µg/ml of the anit-gp120 antibody F105 for 2 hours at 37° C. The cells were then washed in phosphate-buffered saline (PBS), lysed in NP40 buffer and incubated with Protein A-Sepharose beads at 4° C. for 23 hours. Precipitates were analyzed on 7% SDS-polyacrylamide gels after boiling for 3 minutes in sample buffer containing 0.4% β-mercaptoethanol.

Cell surface expression was also assessed by FACS analysis of 293T cells that were either mock-transfected or transfected with pSVIIenv plasmid encoding wild-type or mutant envelope glycoproteins. Cells were incubated for one hour at 4° C., with 0.5 µg of F105, 110.4, C11 or 212A antibodies, washed in PBS, and subsequently incubated with 1 µl/ml phycoerythrin-conjugated goat anti-human IgG (sigma, St. Louis, Mo.). Cells were washed and fixed in 2% formaldehyde in PBS and analyzed on a Becton-Dickenson FACS analyzer.

Computer Analysis

Modeling and visualization of model coiled-coils were done with Slimm, using Silcon Graphics. The illustrations in FIG. 1 were constructed with Molscript (Kraulis, P., *J Appl Crstallogr* 1991).

RESULTS

Introduction of Cysteine Residues into the HIV-1 gp41 Ectodomain

Figure 1A:
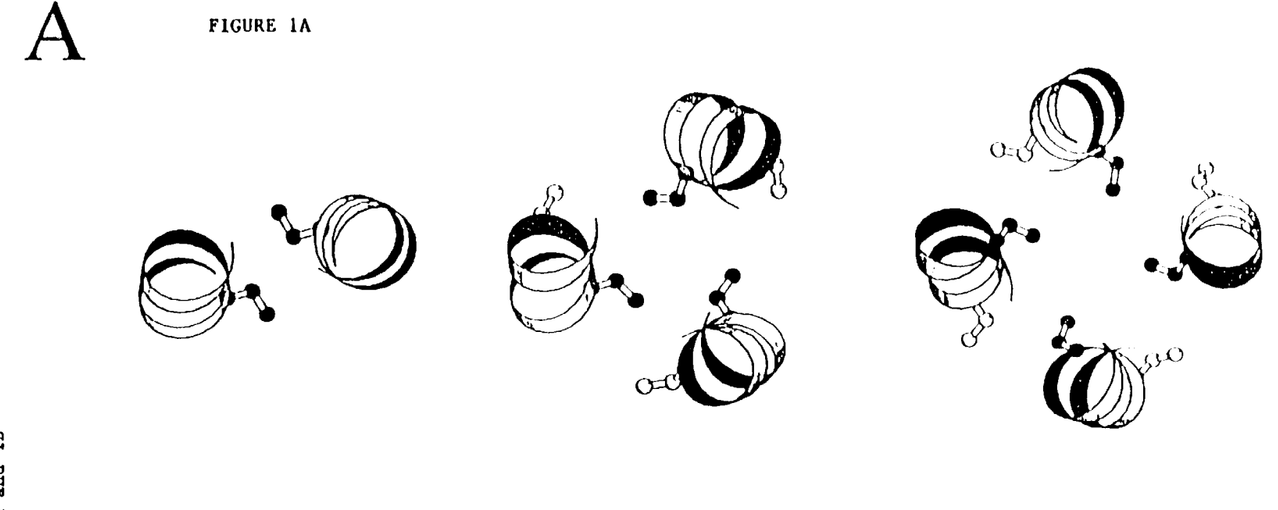
Figure 1B:
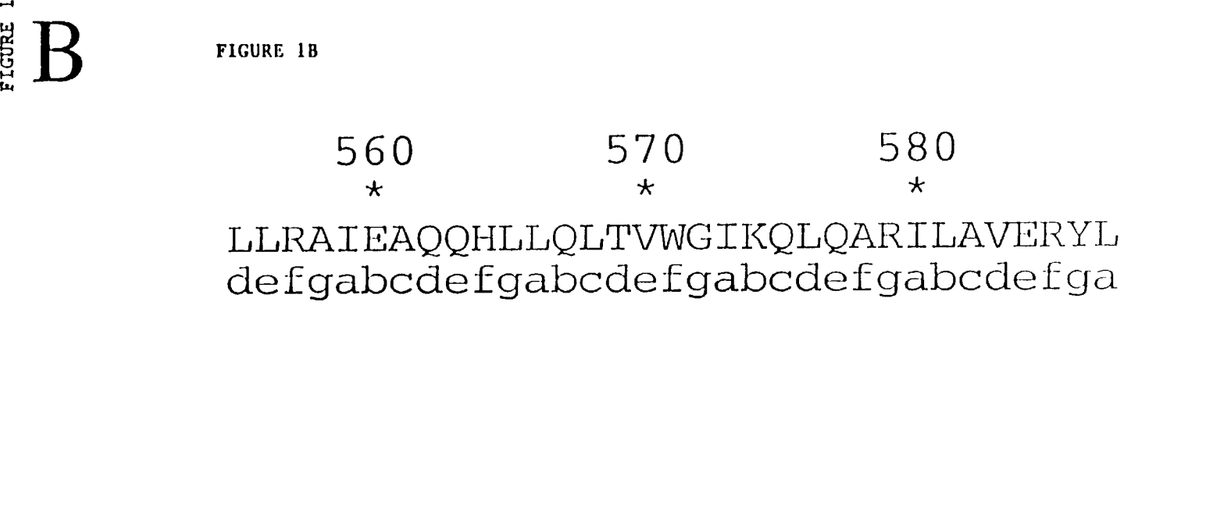

We wished to study whether the introduction of disulfide bonds into the putative sites of contact between the proposed helical coils in the HIV-1 gp41 ectodomain could stabilize the full-length envelope glycoprotein oligomer and allow an analysis of its higher order state. Since at that time this work was initiated, no detailed structure of the HIV-1 gp41 glycoprotein was available, existing dirneric, trimeric and tetrameric coiled coils (O'Shea, E. K., et al. *Science* 539–44 1991; Bullough, P. A., et al., *Nature* 1994; Harbury, P. B., et al., *Science* 1993; Harbury, P. B., et al., *Nature* 1994) were analyzed to predict the optimal positions for placement of cysteine residues (FIG. 1). The distance requirements for the formation of intersubunit disulfide bonds were readily met in theoretical dimeric and tetrameric coiled coils (Hazes, B., et al., *Protein Eng* 1988; Muskal, S. M., et al., *Protein Eng* 1990; Reiter, Y., et al., *Protein Eng* 1995; Sowdhamini, R., *Protein Eng* 1989). In fact, a disulfide bond has been previously introduced in a model dimeric coiled coil by substitution of cysteines at the d position of the helical repeat structure (Zhou, N. E., *Biochemistry* 1993. In the case of the hypothetical tetramer, distance requirements for disulfide bond formation could be met by introduction of cysteines at the g and a positions. In the case of the hypothetical trimer, however, no simple substitution of cysteines met the ideal distance requirements for the formation of a disulfide bond. However, computer modeling of trimeric coiled coils for which crystal structures were available suggested that the introduction of glycerin residues adjacent to the d and e positions of the helix could provide sufficient backbone flexibility to allow the formation of a stale disulfide bond. Table 1 shows the mutant HIV-1 envelope glycoproteins and the observed phenotypes. Most of the envelope glycoproteins were defective in processing of the gp160 precursor tomature gp120 and gp41 glycoproteins (FIG. 1 and data no shown). This suggests that, compared with the wild-type HVI-1 envelope glycoproteins, these mutants exhibit defects either in global folding, in proper exposure of the cleavage site, or in transport of the Golgi apparatus, where envelope glycoprotein cleavage occurs (Earl, P. L., et al., *Proc Natl Acad Sci USA* 1990).

Figure 2:
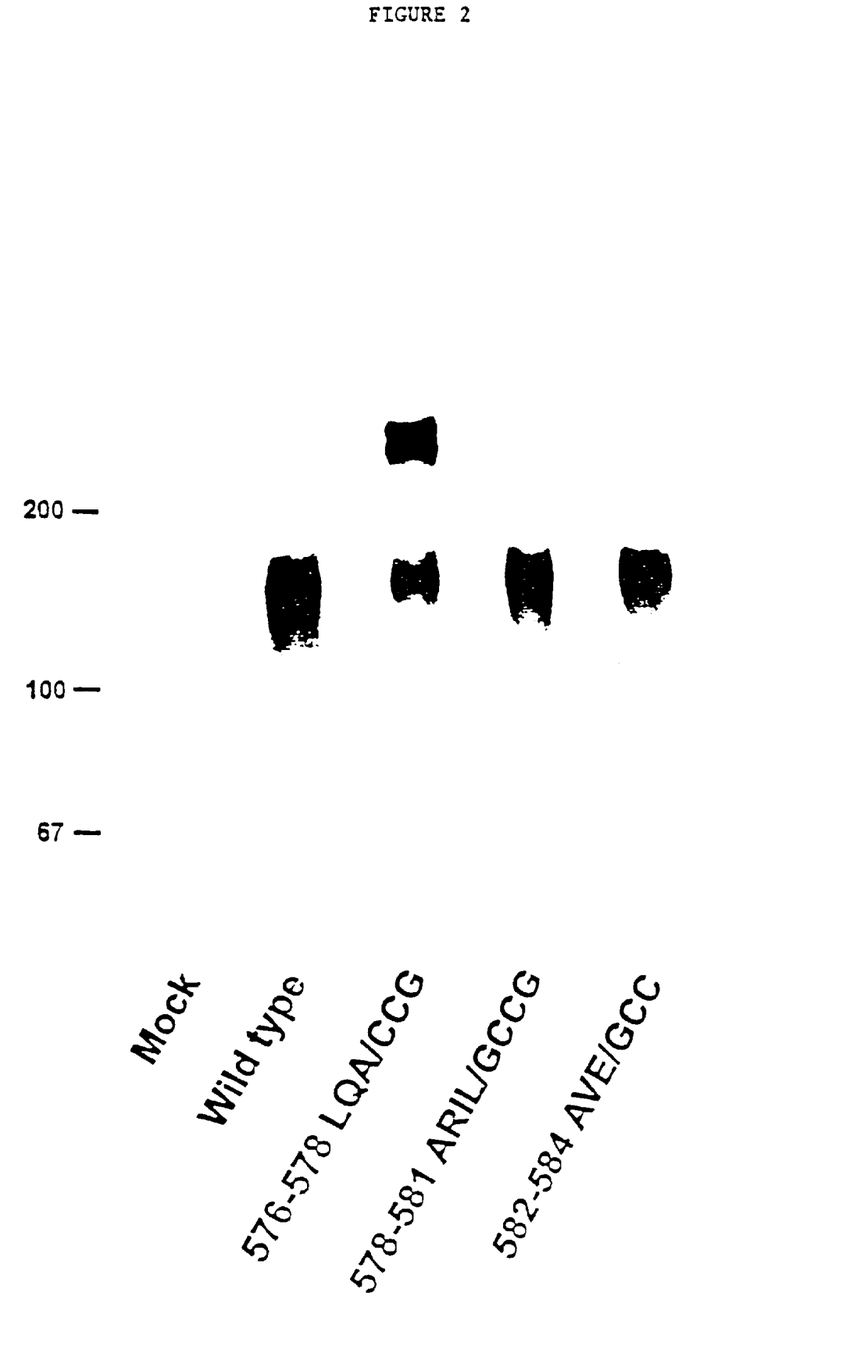
Figure 3:
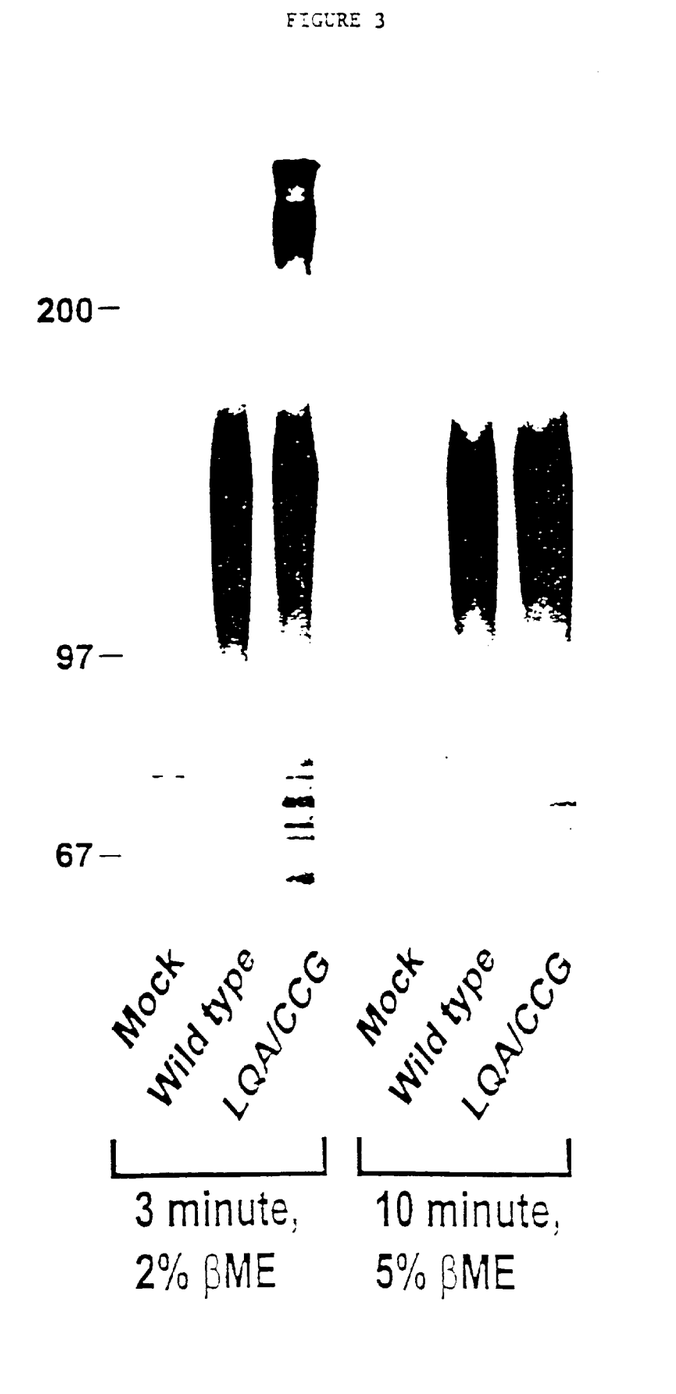
Figure 4:
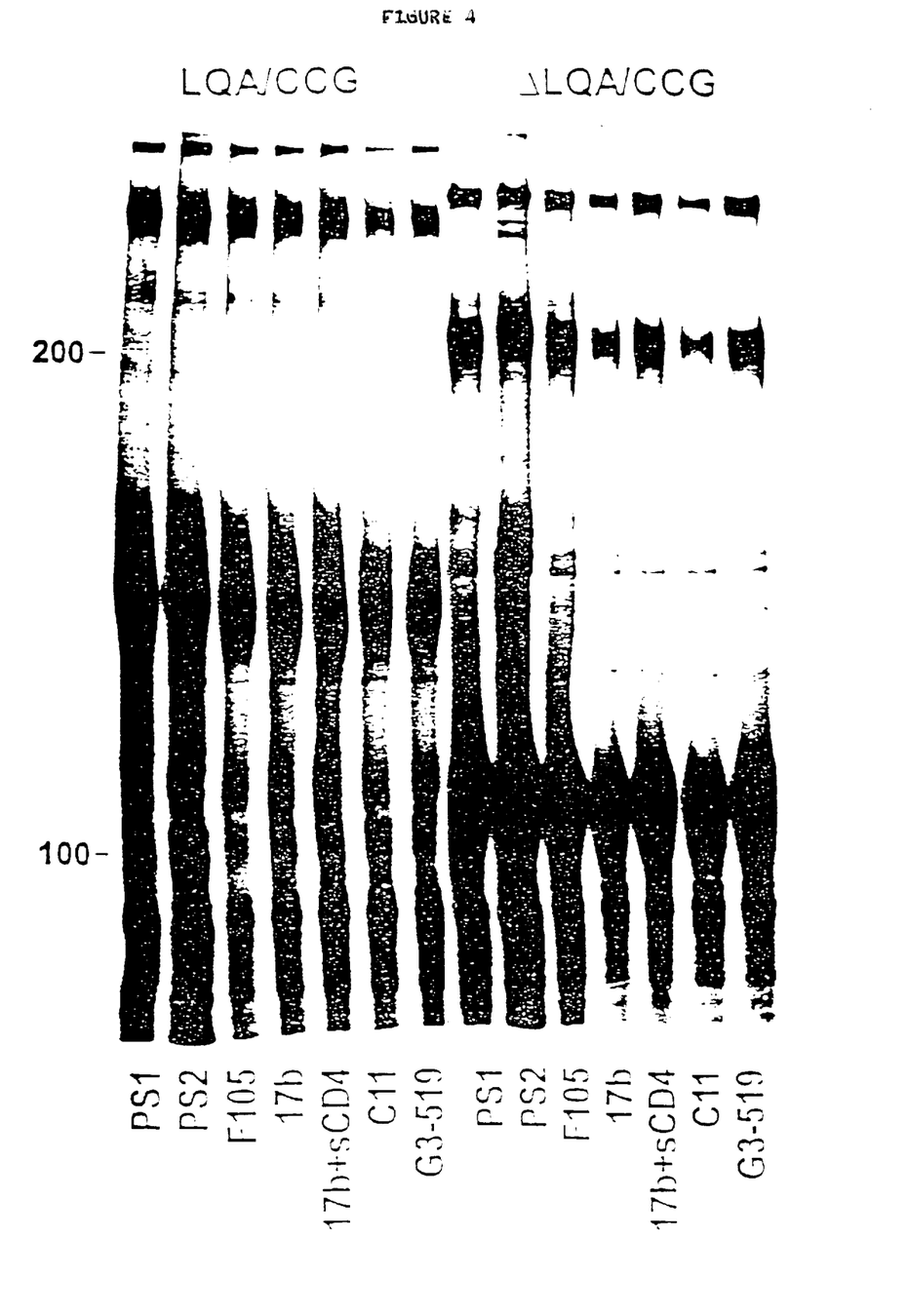

One mutant, 576/7/8 LQA/CCG, (hereafter referred to as LQA/CCG) was notable for the existence of two high molecular weight forms evident on polyacrylamide gels even after boiling or gentle reduction (up to 4% β-mercaptoethanol) (FIG. 2). The same pattern of high molecular weight forms was observed even when iodaacetamide was included in the buffers used for cell lysis and sample preparation (data not shown). Upon boiling the mutant protein in higher concentrations of P-mercaptoethanol, the high molecular weight bands disappeared, with a concomitant increase in the amount of the 160 kD form (FIG. 3). These results are consistent with the formation of higher-order disulfide-linked structures for the mutant gp160 envelope glycoprotein. The cysteines introduced at residues 576 and 577 of this mutant envelope glycoprotein mutant were predicted to form intersubunit disulfide bonds between the d and e positions of a trimeric coiled coil. The conservative substitution of glycine for alanine at position f of the helix (residue 578) was designed to increase the flexibility of the protein backbone in this region. The LQA/CCG mutant was processing-defective when synthesized in transfected COS-1 or HeLa cells and exhibited impaired processing when produced in 293T cells, compared with the wild-type HIV-1 envelope glycoproteins. Nonetheless, the LQA/CCG mutant was expressed on the surface of transfected cells at levels comparable to those of the wild-type envelope glycoproteins, as assessed by FACS analysis and by a surface immunoprecipitation assay (data not shown). Moreover, the higher order forms of the LQA/CCG mutant were precipitated by a number of monoclonal antibodies that recognize discontinuous epitopes on the HIV-1 gp120 envelope glycoprotein (Moore, J. P., et al., *J Virol* 1996). These include the F105 antibody, which recognizes the CD4 binding site, the 17b antibody, which recognizes a CD4-induced epitope, and antibodies directed against the third variable loop of gp120 (FIG. 4 and FIG. 4 legend). It is noteworthy that the 17b epitope represents the discontinuous epitope most sensitive to disruption by detergent (Thaili, M., *J Virol* 1993). These results suggest that the LQA/CCG mutant does not exhibit global defects in folding or transport.

Figure 5:
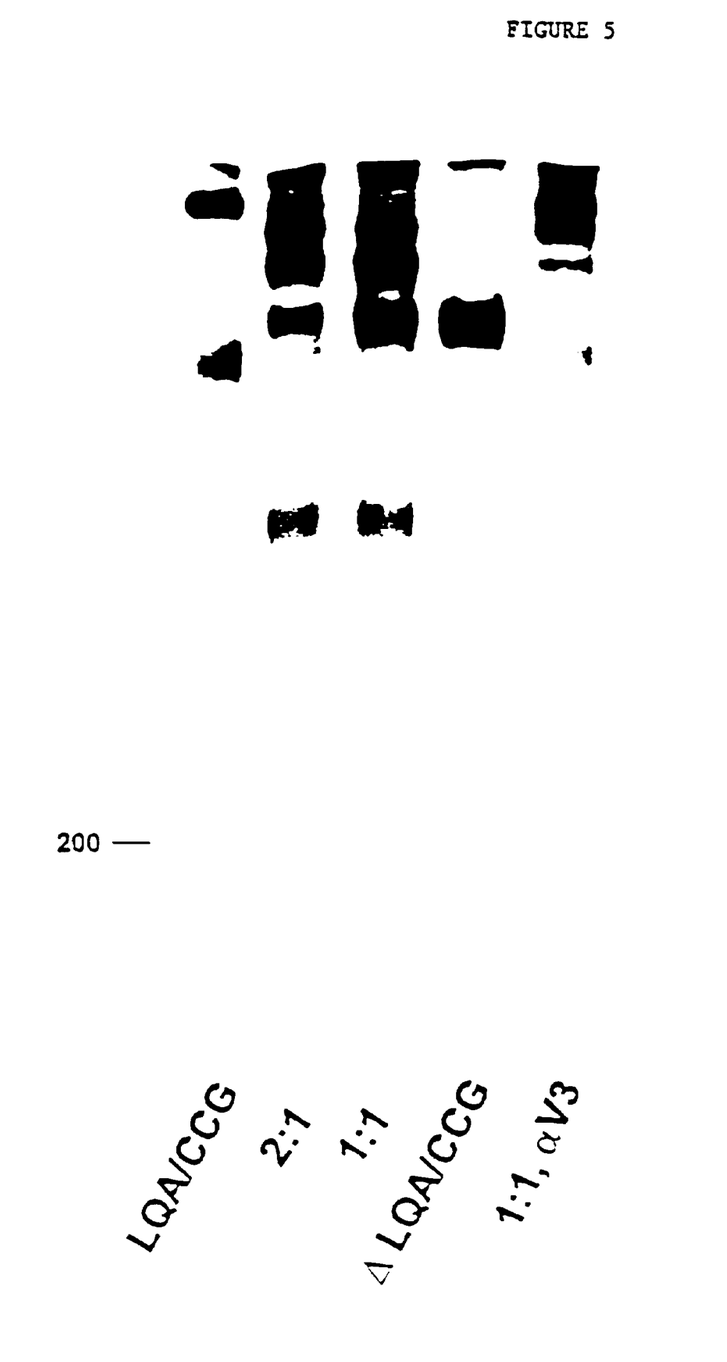

To determine the nature of the higher-order forms observed for the LQA/CCG mutant, a variant of this mutant was created. This variant, AV1/V2/V3 (tail-) 576/7/8 LQA/CCG (hereafter referred to as ΔLQA/CCG, is identical to the LQA/CCG mutant except that it lacks the V1/V2 and V3 gp120 loops and a large portion of the gp41 cytoplasmic tail. These deletions have been shown not to compromise the proper folding or transport of HIV-1 envelope glycoproteins (Wyatt, R., et al., *J Virol* 1995). The ΔLQA/CCG glycoprotein was efficiently expressed on the cell surface as judged by FACS analysis, and was recognized by a number of monoclonal antibodies with conformation-dependent epitopes (FIG. 4 and data not shown). The ΔLQA/CCG envelope glycoprotein precursor migrated with an apparent molecular mass of 110 kD, presumably a monomer, and two apparently higher-order forms resistant to boiling and gentle reduction. The smaller of these higher-order forms migrated slightly slower than the 200 kD marker protein, suggesting that it represents a dimer of the ΔLQACCG protein (FIG. 4). The larger of the two high-order forms of the ΔLQA/CCG protein comigrated with the smaller of the two higher-order forms of the LQA/CCG protein (FIGS. 4 and 5). This is consistent with the expected molecular mass of approximately 330 kD for a ΔLQA/CCG trimer and an expected molecular mass of 320 kD for a LQA/CCG dimer.

To provide additional information about the number of subunits in the observed higher-order forms, the LQA/CCG and ΔLQA/CCG proteins were expressed in the same cells by cotransfection of their respective expresser plasmids. We anticipated that these two proteins would form hetero-oligomers and that the pattern of bands formed would allow a determination of the number of subunits in the assembled oligomers. For example, if the oligomer were a trimer, one would expect to observe two different species of heterotrimers of 380 and 430 kD, in addition to the 480 and 330 kD homotrimers. In addition to the monomers and 220 and 320 kD homodimers, a heterodimer of 270 kD would be expected. Markedly different patterns of hetero-oligomers would be observed if the assembled oligomer were a tetramer.

The results of coexpressing the LQA/CCG and ΔLQA/CCG proteins in 293T cells are shown in FIG. 5, lanes 2 and 3. By varying the ratios of the cotransfected plasmids, the pattern of intensity of the observed bands was altered, helping to confirm the identity of the proteins in each band. The LQA/CCG and ΔLQA/CCG proteins were transfected alone in the experiments in lanes 1 and 4 respectively. In lane 2, the LQA/CCG and ΔLQA/CCG mutants were expressed using a two:one ratio of plasmids encoding these constructs. In lane 3, equal amounts of each plasmid were transfected. The pattern of bands corresponds precisely to that expected for a trimer. The density of the heterotrimeric forms reflects that expected from the relative expression of each of the mutants present in the transfected cell. The identity of the components in each band was further confirmed by precipitating the lysate shown in lane 3 with an antibody, 110.3, against the gp 120 V3 loop (FIG. 5, lane 5). As expected, this antibody recognized only oligomeric forms proposed to contain the LQA/CCG protein. The decreasing order of efficiency with which the 110.3 antibody precipitated the 480, 430, 380 and 330 kD proteins is consistent with the proposed content of 3,2,1 and 0 LQA/CCG monomers, respectively, in the trimer. We conclude that the LQA/CCG and ΔLQA/CCG proteins form disulfide bonds to stabilize a trimer.

REFERENCES

Alkhatib, G., Combadiere, C., Broder, C. C., et al., *Science* 272:1955–1958.
Barre-Sinoussi, F., Chermann, J. C., Rey, F., et al., *Science* 220:868–71 (1983).
Broder, C. C., Earl, P. L., Long, D., *Proc Natl Acad Sci USA* 91:11699–703 (1994).
Bullough, P. A., Hughson, F. M., Skehel, J. J., et al., *Nature* 371:37–43 (1994)
Cao, J., Bergeron, L., Helseth, E., et al., *J Virol* 67:2747–2755.
Carr, C. M., Kim, P. S., *Cell* 73:823–832 (1993).
Chan, D. C., Fass, D., Berger, J. M., et al., *Cell* 89:263–273 (1997).
Choe, H., Farzan, M., Sun, Y., et al., *Cell* 85:1135–1148.
Dalgleish, A. G., Beverley, P. C., Clapham, P. R., et al., *Nature* 312:763–767.
Deng, H., Liu, R., Ellmeier, W., et al., *Nature* 381:661–666 (1996).
Doranz, B. J., Rucker, J., Yi, Y., et al., *Cell* 85:1149–1158 (1996).
Dragic, T., Litwin, V., Allaway, G. P., *Nature* 381:667–673 (1996).
Earl, P. L., Moss, B., Doms, R. W., *J Virol* 65:2047–2055 (1991).
Earl, P. L., Doms, R. W., Moss, B., *Proc Natl Acad Sci USA* 87:648–652 (1990).
Fauci, A. S., Macher, A. M., Longo, D. L., et al., *Ann Intem Med* 100:92–106 (1984).
Feng, Y., Broker, C. C., Kennedy, P. E., et al., *Science* 272:872–877 (1996).
Freed, E. O., Myers, D. J., Risser, R., *Proc Natl Acad Sci USA* 87:4650–4654.
Gallo, R. C., Salahuddin, S. Z., Popovic, M., et al., *Science* 224:500–503 (1984).
Harbury, P. B., Zhang, T., Kim, P. S., et al., *Science* 262:1401–1407 (1993).
Harbury, P. B., Kim, P. S., Alber T., *Nature* 371:80–83 (1994).
Hazes, B., Dijkstra, B. W., *Protein Eng* 2:119–125 (1988).
Helseth, E., Kowalski, M., Gabuzda, D., et al., *J Virol* 64:2416–2420 (1990).
Klatzmann, D., Champagne, E., Chamaret, S., et al., *Nature* 312:767–768 (1984).
Kowalski, M., Potz, J., Basiripour, L., et al., *Science* 237:1351–1355 (1987).
Kraulis, P., *J Appl Crystallogr* 24:924–950 (1991).

Leonard, C. K., Spellman, M. W., Riddle, L., et al., *J Biol Chem* 265:10378–10382.
Lu, M., Blacklow, S. C., Kim, P. S., *Nat Struct Biol* 2:1075–1082 (1995).
Mammano, F., Kondo, E., Sodroski, J., et. al., *J Virol* 64:2416–2420 (1990).
Moore, J. P., Sodroski, J., *J. Virol* 70:1863–1872 (1996).
Muskal, S. M., Holbrook, S. R., Kim, S. H. *Protein Eng* 3:667–672 (1990).
O'Shea, E. K., Klemm, J. D., Kim, P. S., et al., *Science* 254:539–544 (1991).
Pinter, A., Honnen, W. J., Tilley, S. A., et al. *J Virol* 63:2674–1679 (1989).
Reiter, Y., Brinkmann, U., Jung, S. H., et al., *Protein Eng* 8:1323–1331 (1995).
Schawaller, m., Smith, G. E., Skehel, J. J., et al., *Virology* 172:367–369 (1989).
Sowdhamini R., Srinivasan, N., Shoichet, B., *Protein Eng* 3:95–103 (1989).
Thali, M., Moore, J. P., Furman, C., et al., *J Virol* 67:3979–3988 (1993).
Trkola, A., Dragic, T., Arthos, J., et al., *Nature* 384:184–87 (1996).
Wu, L., Gerard, N. P., Wyatt, R., et al., *Nature* 184:179–183 (1996).
Wyatt, R., Moore, J., Accola, M., et al., *J Virol* 64:2416–2420 (1990).
Zhou, N. E., Kay, C. M., Hodges, R. S., *Biochemistry* 32:3178–3187 (1993).

All references described in the above specification are incorporated herein by reference.

Table 1 HIV-Envelope Glycoprotein Mutants and Phenotypes. The HIV-1 enevlope glycoprotein mutants, the location of the cysteines in the heptad repeat and the presence of higher order forms after boiling for 3 minutes in the presence of 0.2% β-mercaptoethanol are shown.

| Construct | | Heptad Position | High Order Forms |
|---|---|---|---|
| 569 | T/C | d | – |
| 583 | V/C | d | – |
| 586–587 | YL/CC | ga | – |
| 564–567 | HLLQ/GCCG | ga | – |
| 568–570 | LTV/GCC | de | – |
| 571–574 | WGIK/GCCG | ga | – |
| 576–578 | LQA/CCG | de | + |
| 578–581 | ARIL/GCCG | ga | – |
| 582–584 | AVE/GCC | de | – |
| 585–588 | RYLK/GCCG | ga | – |
| 583–585 | VER/CCG | de | – |

We claim:

1. An isolated and purified protein encoded by nucleotide sequence encoding a modified HIV-1 or HIV-2 envelope glycoprotein containing at least:
   i) a coiled coil portion of a gp41 transmembrane glycoprotein, wherein said coiled coil has a heptad repeat wherein each of said seven consecutive amino acid residues are designated a, b, c, d, e, f, and g corresponding to amino acid sequences selected from a group consisting of amino acids 555–561, 562–568, 569–575, 576–582 and 583–589 of SEQ ID NO: 11, wherein at least two amino acids in positions "a", "d" and "e" have been substituted by cysteine residues, and "f" is glycine; and
   ii) a gp120 glycoprotein or a gp120 derivative, wherein the gp120 derivative contains multiple gp120 constant regions connected by variable regions and/or linker residues that permit potential turns in the polypeptide structure so that the derivative maintains a conformation approximating that of a wild type gp120, wherein at east a portion of one variable region has been deleted.

2. The protein of claim 1, wherein "d" and "e" position of the coiled coil helix, d/e, corresponds to sites numbered 555/556, 562/563, 569/570, 576/577 or 583/584 of SEQ ID NO: 11.

3. The protein of claim 1, wherein a Gly is substituted for Ala at position "f" of the coiled coil helix.

4. The protein of claim 3, wherein the "f" position of the coiled coil helix corresponds to sites numbered 557, 564, 571, 578 and 585 of the SEQ ID NO: 11.

5. The protein of claim 3, wherein the Gly is substituted for Ala in the "f" positions of the coiled coil helix corresponding to sites 576, 577 and 578 in the SEQ ID NO: 11.

* * * * *

SEQUENCE LISTING

<160> NUMBER OF SEQ ID NOS: 11

<210> SEQ ID NO 1
<211> LENGTH: 38
<212> TYPE: DNA
<213> ORGANISM: Human immunodeficiency virus type 1

<400> SEQUENCE: 1
cagcatctgt tgcagctgtg tgcttggggc acaagcag         38

<210> SEQ ID NO 2
<211> LENGTH: 39
<212> TYPE: DNA
<213> ORGANISM: Human immunodeficiency virus type 1

<400> SEQUENCE: 2
caagcaagaa tcctagcctg tgaaaggtac ctaaaggat        39

<210> SEQ ID NO 3
<211> LENGTH: 42
<212> TYPE: DNA
<213> ORGANISM: Human immunodeficiency virus type 1

<400> SEQUENCE: 3
agaatcctag ctgtggagcg ctgctgtaag gatcaacagc tc    42

<210> SEQ ID NO 4
<211> LENGTH: 48
<212> TYPE: DNA
<213> ORGANISM: Human immunodeficiency virus type 1

<400> SEQUENCE: 4

```
gctattgagg cgcaacaggg ttgctgcggt ctcacagtct ggggcatc          48

<210> SEQ ID NO 5
<211> LENGTH: 54
<212> TYPE: DNA
<213> ORGANISM: Human immunodeficiency virus type 1

<400> SEQUENCE: 5
attgaggcgc aacagcacct gctgcaaggc tgctgctggg gcatcaagca gctc    54

<210> SEQ ID NO 6
<211> LENGTH: 46
<212> TYPE: DNA
<213> ORGANISM: Human immunodeficiency virus type 1

<400> SEQUENCE: 6
ttgcaactca cagtcggggt gctgtggcca gctccaagca agaatc              46

<210> SEQ ID NO 7
<211> LENGTH: 48
<212> TYPE: DNA
<213> ORGANISM: Human immunodeficiency virus type 1

<400> SEQUENCE: 7
gtctggggca tcaagcagtg ctgcggaaga attctagctg tggaaaga          48

<210> SEQ ID NO 8
<211> LENGTH: 48
<212> TYPE: DNA
<213> ORGANISM: Human immunodeficiency virus type 1

<400> SEQUENCE: 8
atcaagcagc tccaaggatg ctgcggcgcc gtggaaagat acctaaag          48

<210> SEQ ID NO 9
<211> LENGTH: 48
<212> TYPE: DNA
<213> ORGANISM: Human immunodeficiency virus type 1

<400> SEQUENCE: 9
caagcaagaa tcctaggttg ttgtagatat ctaaaggatc cacagctc          48

<210> SEQ ID NO 10
<211> LENGTH: 48
<212> TYPE: DNA
<213> ORGANISM: Human immunodeficiency virus type 1

<400> SEQUENCE: 10
agaatcctag ctgtggaagg atgctgcggt gatcaacagc tcgggatt          48

<210> SEQ ID NO 11
<211> LENGTH: 33
<212> TYPE: PRT
<213> ORGANISM: Human immunodeficiency virus type 1

<400> SEQUENCE: 11

Leu Leu Arg Ala Ile Glu Ala Gln Gln His Leu Leu Gln Leu Thr Val
1               5                   10                  15

Trp Gly Ile Lys Gln Leu Gln Ala Arg Ile Leu Ala Val Glu Arg Tyr
            20                  25                  30

Leu
```